(12) United States Patent
Stessman

(10) Patent No.: US 6,584,355 B2
(45) Date of Patent: Jun. 24, 2003

(54) SYSTEM AND METHOD FOR MEASURING BATTERY CURRENT

(75) Inventor: Nicholas J. Stessman, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 94 days.

(21) Appl. No.: 09/829,825

(22) Filed: Apr. 10, 2001

(65) Prior Publication Data

US 2002/0163991 A1 Nov. 7, 2002

(51) Int. Cl.[7] .......................... A61N 1/36; A61N 1/378; A61N 1/37
(52) U.S. Cl. ............................. 607/29; 607/7
(58) Field of Search .................. 607/7, 9, 29

(56) References Cited

U.S. PATENT DOCUMENTS

| | | | |
|---|---|---|---|
| 4,488,555 A | 12/1984 | Imran | 128/419 PT |
| 4,556,061 A | 12/1985 | Barreras et al. | 128/419 PT |
| 4,712,179 A | * 12/1987 | Heimer | 364/417 |
| 5,137,020 A | 8/1992 | Wayne et al. | 128/419 PS |
| 5,137,021 A | 8/1992 | Wayne et al. | 128/419 PT |
| 5,391,193 A | 2/1995 | Thompson | 607/29 |
| 5,458,624 A | 10/1995 | Renirie et al. | 607/29 |
| 5,769,873 A | 6/1998 | Zadech | 607/29 |
| 6,148,235 A | 11/2000 | Kuiper | 607/29 |

\* cited by examiner

*Primary Examiner*—Carl Layno
(74) *Attorney, Agent, or Firm*—Schwegman, Lundberg, Woessner & Kluth, P.A.

(57) ABSTRACT

Systems, devices and methods are provided for measuring battery current. According to one aspect, a medical device is provided that comprises a battery, a pulse generator, and a current measuring device. The pulse generator draws a pulse generator current from the power source, and the current measuring device determines the pulse generator current or tracks charge depletion from the battery. The current measuring device comprises an oscillator and a counter. The oscillator produces an oscillating output with a frequency of oscillation dependent on the pulse generator current, and the counter provides an oscillation count for the oscillating output. The current measuring device is capable of being calibrated while continuously determining the pulse generator current. In one embodiment, the current measuring device includes at least two current sources, each including an operational amplifier that has an autozeroing feature.

44 Claims, 8 Drawing Sheets

SYSTEM AND METHOD FOR MEASURING BATTERY CURRENT

FIELD OF THE INVENTION

This invention relates generally to the field of medical devices, and more particularly to systems, devices, methods and applications for measuring current drain or charge depletion for medical devices.

BACKGROUND

Medical devices, including cardiac stimulus devices such as implantable cardiac pacemakers and implantable cardioverter defibrillators (ICDs), are surgically implanted within a patient. Cardiac stimulus devices have one or more electrical leads with one or more electrodes that conduct signals to and receive signals from the patient's heart. As such, cardiac stimulus devices provide electrical therapy to the patient. A programming device or programmer is able to communicate with the medical device through a communication link. The communication link provides means for commands and data to be transmitted and received between the programmer and the device.

Longevity is an important aspect regarding the performance of the medical device, and it is determined primarily by the capacity of the battery and the current drain of the electronics; i.e. battery status. The current drain depends on a number of variables, including the impedance(s) of the pacing lead(s), the ratio of sensed beats to paced beats, the background current of the device's electronics, and the characteristics of the pacing pulse(s) such as pacing rate, pacing mode, amplitude and width. Approximations for current drain and/or charge depletion for the medical device are obtained by estimating these variables. However, estimating these variables is difficult because they vary over the lifetime of the device. Tradeoffs that sacrifice the longevity of the medical device for the safety of the patient may be required to maintain an appropriate safety margin that accounts for the granularity and uncertainty in estimating these variables.

Latent electrical faults within the implanted device may cause elevated current drains. These electrical faults can go undetected early on in the life of an implanted device without a means for measuring and reporting the current of the implanted device. A problem with reporting current measurements for an implanted device is that the communication system, such as a telemetry circuit, draws considerably more current during a communication session than in a quiescent period. This extra current drawn by the telemetry circuit can adversely affect the current measurements.

Therefore, there is a need in the art to provide a system and method for measuring the current drain or charge depletion for implantable medical devices, and to provide applications for determining the battery status, detecting electrical faults, and reporting the battery current.

SUMMARY OF THE INVENTION

The present subject matter addresses the aforementioned problems by providing systems, devices and methods for measuring current drain and tracking the charge depletion. Applications include a method for determining battery status, for determining potential faults, and for displaying or reporting current drain.

One aspect provides a medical device, comprising a battery, a pulse generator, an electrode system, and a current measuring device. The pulse generator draws a pulse generator current from the battery. The electrode system is in electrical communication with the pulse generator and applies electrical therapy, such as pacing pulses, to a patient. The current measuring device determines the pulse generator current, and is capable of being calibrated as it is determining the pulse generator current. Therefore, the current measuring device is able to continuously measure or track the current drain from the battery and still be calibrated or periodically calibrated to maintain the accuracy of these current measurements.

One embodiment of the current measuring device comprises an oscillator and a counter. The oscillator produces an oscillating output that has a frequency of oscillation dependent on the pulse generator current, and the counter provides an oscillation count for the oscillating output, i.e. the counter counts the number of oscillations in the oscillation output over a known time interval. The pulse generator current is determined from the oscillation count.

One embodiment of the current measurement device comprises a current source that provides an oscillator input current that is dependent on the pulse generator current to the oscillator. One current source embodiment includes a current divider for dividing current drawn from the battery into the pulse generator current and an attenuated current. The current divider includes a sense resistor, an attenuation resistor, and an operational amplifier. The pulse generator current flows through the sense resistor, and the attenuated current flows through the attenuation resistor. The operational amplifier applies negative feedback to provide a voltage drop across the attenuation resistor that is substantially equal to the voltage across the sense resistor.

In another embodiment, the device also includes a second current source having a second operational amplifier. Both operational amplifiers have an autozeroing feature that compensates for an offset voltage that could adversely affect the value of the attenuated current, and thus adversely affect the determination of the pulse generator current. The pulse generator current is continuously measured using one of the two current sources. As one current source autozeros, the other current source continues to operate.

Another aspect provides a method for determining current drain for a medical device, wherein the oscillations are counted for a period of time, and the pulse generator current is determined by the oscillation count over the period of time. Another aspect provides a method for tracking charge depletion of a battery in an implantable medical device, wherein the charge depletion of a battery is determined by continuously summing the oscillation count over successive periods of time.

These and other aspects, features, embodiments, applications, and advantages of the invention will become apparent from the following description of the preferred embodiments of the invention.

DETAILED DESCRIPTION

Figure 1:
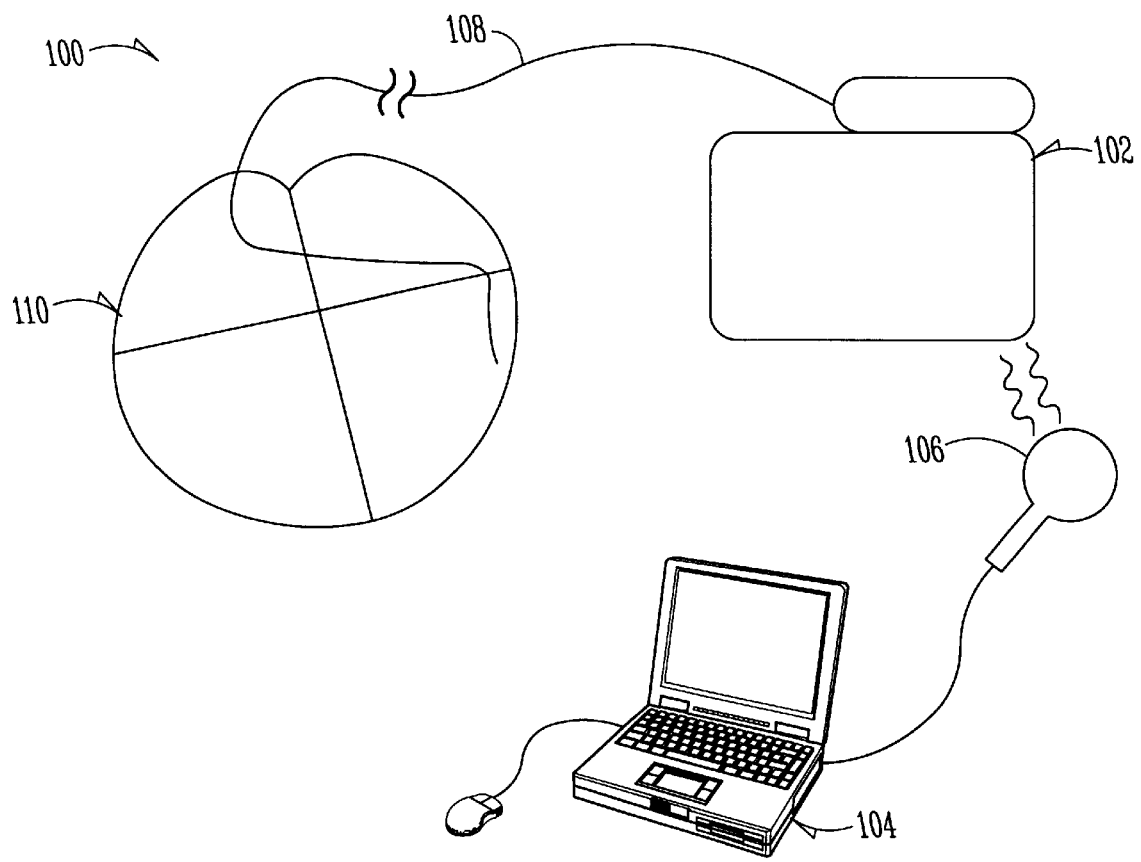
FIG. 1 is a schematic view of one system embodiment.

The present subject matter addresses the aforementioned problems, and provides systems, devices and methods for measuring battery current and tracking charge depletion of a battery. In the following detailed description, references are made to the accompanying drawings that illustrate specific embodiments in which the invention may be practiced. In the drawings, like numerals describe substantially similar components throughout the several views. Changes in the electrical, mechanical, structural, logical or programming designs may be made to the embodiments without departing from the spirit and scope of the present invention. The following detailed description is, therefore, not to be taken in a limiting sense and the scope of the present invention is defined by the appended claims and their equivalents.

FIG. 1 illustrates a cardiac rhythm management system 100, which generally comprises a medical device 102 and a programmer device 104 capable of communicating with the medical device 102 through a communication channel 106 such as that which may be created using induction coils or radio frequency telemetry, for example. The medical device 102 has an electrode system 108 for providing therapy; i.e. for delivering electrical pulses produced by the pulse generator to a patient's heart 110 and for sensing intrinsic electrical pulses produced by the patient's heart 110. Commands and data, including both raw and processed data, are capable of being communicated between the medical device 102 and programmer device 104. Raw data is processed using circuitry, software programs, or a combination thereof, in the medical device 102, in the programmer device 104, or in both devices.

Figure 2:
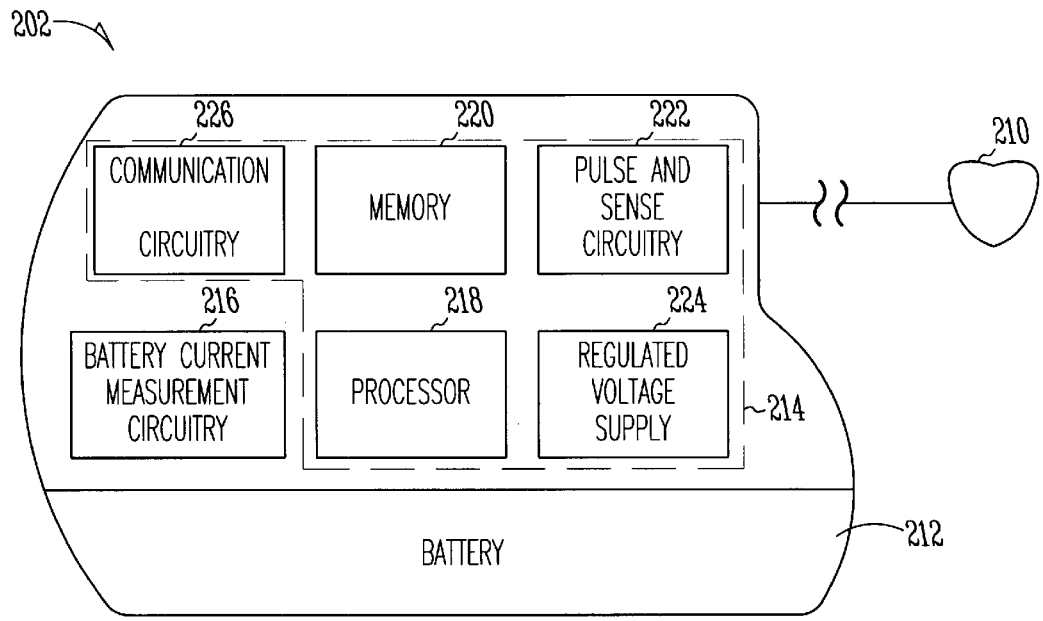
FIG. 2 is a block diagram for one medical device embodiment.

FIG. 2 shows a medical device 202 that generally comprises a power source 212 such as a battery, a pulse generator 214, and a current measuring device or battery current measurement circuitry 216. The pulse generator 214 draws a pulse generator current from the power source 212, and the current measuring device 216 determines the pulse generator current. In one embodiment, the current measurement device 216 determines the average pulse generator current over a period of time. In another embodiment, the current measuring device 216 determines the total charge depletion of the power source 212. In other embodiments, the current measuring device 216 is implemented in applications or methods for determining battery status, for detecting potential faults, and applications for displaying current drain. These applications are described below.

As indicated in FIG. 2, one embodiment of the pulse generator 214 comprises a processor 218, a memory portion 220 operably connected to the processor 218, a pulse and sense portion 222 operably connected to the processor 218 for delivering and receiving electrical pulses to and from the heart 210, a regulated voltage supply 224, and a communication portion 226 operably connected to the processor 218 for communicating with a programmer device 104. The pulse generator 214 forms a pulse generator load that draws a pulse generator current from the battery 212. The current measuring device 216 provides means for determining the pulse generator current, which in one embodiment includes means for determining the average pulse generator current, and in another embodiment includes means for tracking charge depletion in the battery 212.

Figure 3:
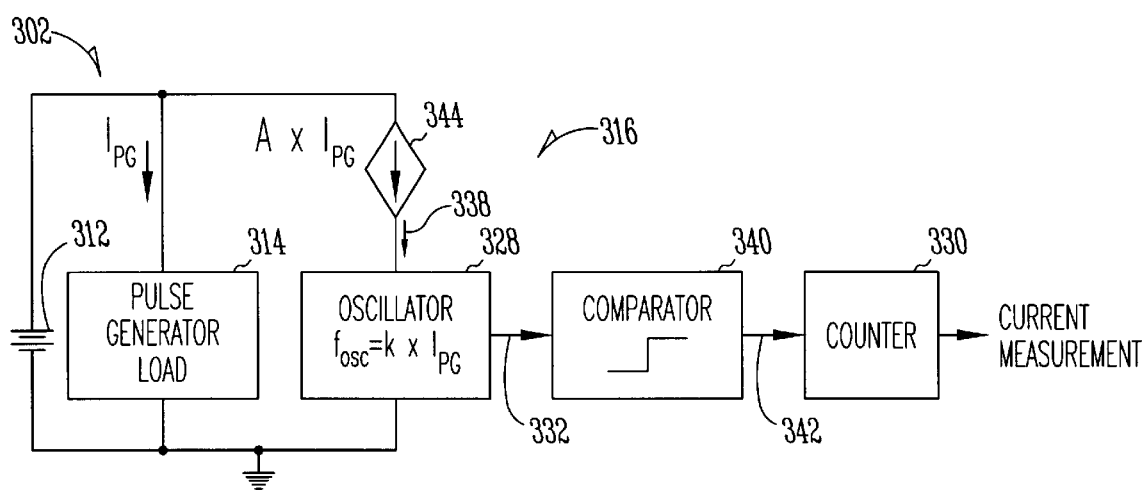
FIG. 3 is a block diagram of the electronic circuitry for the medical device of FIG. 2.

FIG. 3 illustrates electronic circuits for the medical device 302, and shows one embodiment of the current measuring device 316 that includes an oscillator 328 and a counter 330. The oscillator 328 produces an oscillating output 332, which has a frequency of oscillation dependent on the pulse generator current $I_{PG}$ that the pulse generator load 314 draws from the battery 312. This frequency of oscillation is represented by the equation: $f_{osc}=k \times I_{PG}$. The counter 330 provides or determines an oscillation count for the oscillating output 332, i.e. the counter 330 counts the oscillations of the oscillation output 332. The pulse generator current $I_{PG}$ is determined from the oscillation count through a data process that may occur in the medical device, the programmer device, partially in both devices, or even in another processing device. Thus, the oscillator 328 provides means for providing an oscillating output 332 with a frequency of oscillation that is dependent on the pulse generator current $I_{PG}$, and the counter 330 provides means for providing or determining an oscillation count for the oscillating output 332.

One embodiment of the current measuring device 316 further includes a comparator 340. The comparator 340 receives the oscillating output 332 from the oscillator 328 and generates a corresponding oscillating comparator output 342 that is received by the counter 330.

One embodiment of the medical device 302, as illustrated in FIG. 3, includes a current source 344 that provides an oscillator input current 338 for the oscillator 328. This oscillator input current 338 is dependent on the pulse generator current $I_{PG}$, and thus provides means for providing an oscillator input current 338 to the oscillator 328 that is dependent on the pulse generator current $I_{PG}$. FIG. 3 shows that the current source 344 provides an oscillator input current 338 that is proportional to the pulse generator current $I_{PG}$, i.e. "$A \times I_{PG}$".

Figure 4:
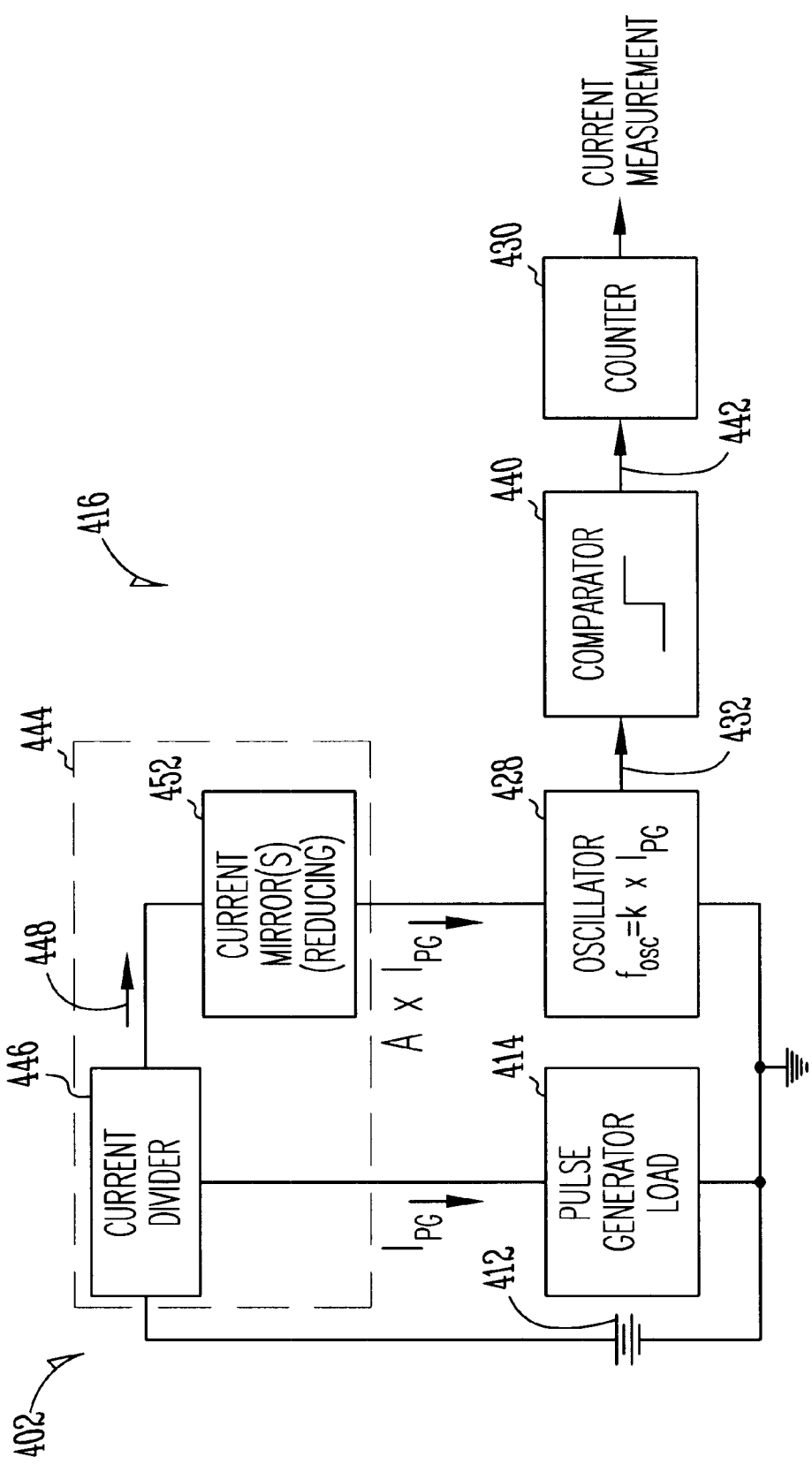
FIG. 4 is a block diagram of the electronic circuitry for the medical device of FIG. 2.

FIG. 4 illustrates electronic circuitry for the medical device 402 that includes the battery 412, the pulse generator load 414 and the current measuring device 416. FIG. 4 shows one embodiment of the current source 444 that includes a current divider 446 for dividing current drawn from the battery 412 into the pulse generator current $I_{PG}$, and an attenuated current 448. The attenuated current 448 is small enough so as not to substantially increase the current drain from the battery and thus the life of the medical device, and so as not to adversely affect the operation of the medical device by limiting the pulse generator current $I_{PG}$. One embodiment of the current source 444 that also includes current mirror stages 452 that further reduce the current as desired for the characteristics of a particular oscillator 428. FIG. 4 also shows that the current measuring device 416 includes an oscillator 428, a comparator 440 and a counter 430, which were previously described with respect to FIG. 3.

Figure 5:
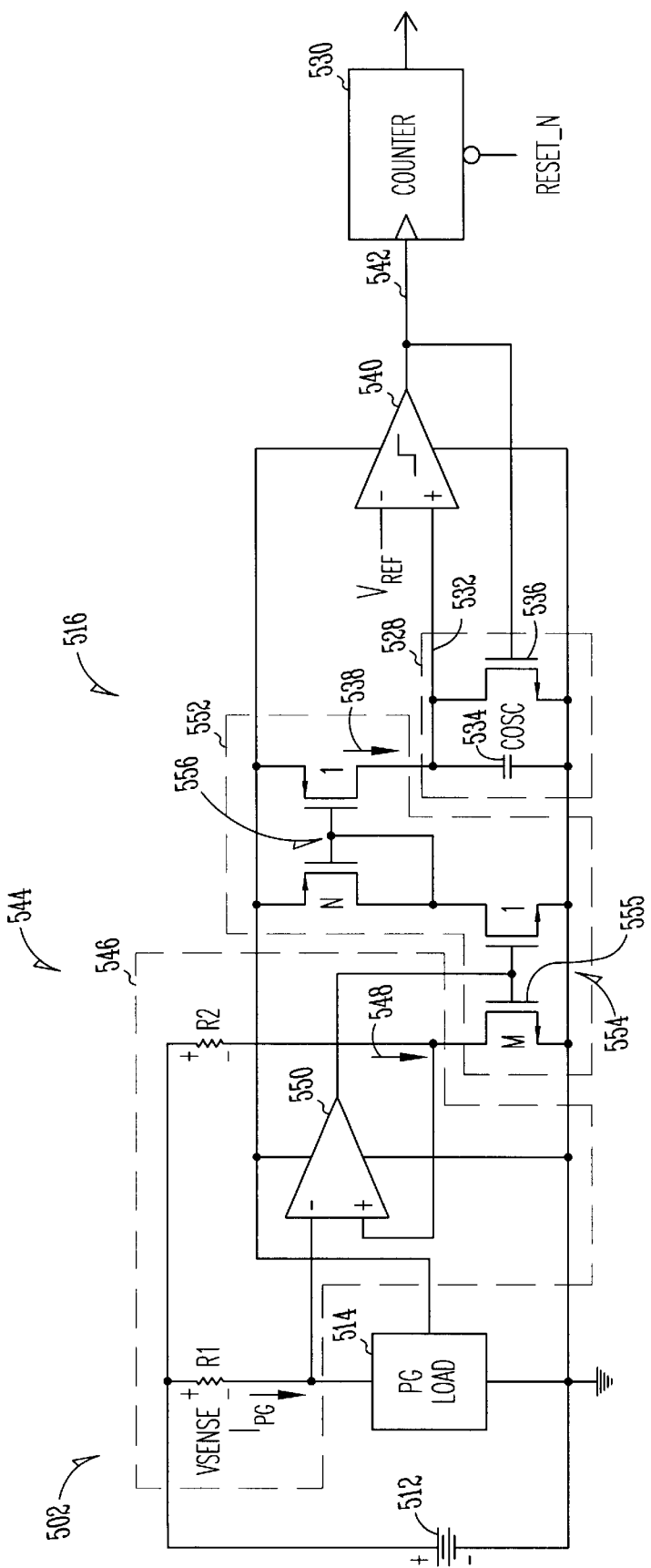
FIG. 5 is a schematic of the electronic circuitry according to the block diagrams of FIGS. 3 and 4.

FIG. 5 is a schematic of the electronic circuitry according to the block diagram of FIGS. 3 and 4. One embodiment of the current divider 546 includes a sense resistor R1 through which the pulse generator current $I_{PG}$, flows, an attenuation resistor R2 through which the attenuated current 548 flows, and an operational amplifier 550 which applies negative feedback to provide a voltage drop across the attenuation resistor R2 that is substantially equal to the voltage across the sense resistor R1.

The current mirror stages 552 include a first current mirror stage 554 for receiving the attenuated current 548 and a second current mirror stage 556 for providing the oscillator input current 538. The first current mirror stage 554 provides an additional M-to-1 current reduction and the second current mirror stage 556 provides an additional N-to-1 current reduction in the oscillation input current 538. Therefore, the current mirrors 554 and 556 further attenuate the signal by a factor of M×N as desired for the oscillating characteristics of the chosen oscillator 528. Thus, in the illustrated embodiment that includes both the current divider 546 and the current mirrors 552, the oscillator input current 538 is represented by the following equation.

$$\text{Oscillator Input Current} = A \times I_{PG} = [(R1)/(R2 \times M \times N)] \times I_{PG}$$

One embodiment of the oscillator 528 comprises a capacitor 534, a reset switch 536, and a comparator 540. The capacitor 534 is charged by an oscillator input current 538 that is dependent on the pulse generator current $I_{PG}$. The reset switch 536 discharges the capacitor 534 when the voltage across the capacitor 534 increases to a level approximately equal to a reference voltage $V_{REF}$. The comparator 540 compares a voltage across the capacitor 534 with the reference voltage $V_{REF}$, and provides a resulting oscillating comparator output 542 to the counter 530.

The counter 530, in one embodiment, is capable of being periodically reset using a reset strobe, represented by the RESET_N input line, that is derived from a known, stable time base such as a crystal oscillator. As will be discussed in more detail below by way of example, resetting the counter 530 provides means for collecting oscillation counts over one or more periods of time to determine the pulse generator current, or for collecting oscillation counts over the lifetime of a battery 512 to track the charge depletion of the battery 512.

For the illustrated oscillator 528, the frequency of the oscillating output 532, and thus of the oscillating comparator output 542, is determined by the following equations:

$$f_{osc} = (\text{Oscillator Input Current})/(C_{osc} \times V_{ref});$$

$$f_{osc} = (A * I_{PG})/(C_{osc} \times V_{ref}); \text{ and}$$

$$f_{osc} = I_{PG} \times [(R1)/((C_{osc} \times V_{ref}) \times (M \times N \times R2))].$$

For example, if $I_{PG}$ is 10 micro amperes, R1 is 250 ohms, R2 is 250 k ohms, $V_{REF}$ is one volt, $C_{OSC}$ is 50 picofarads, and M×N=20, the output frequency of the oscillator is 10 Hz. These values provide the circuit with a convenient 1 microampere per Hertz scale factor. The counter 530 measures the output frequency by counting the oscillations from the comparator 540 for a time period. The digital counter can be reset periodically with RESET_N, which is generated from a known, stable time base (i.e. a crystal oscillator).

The above-described circuit provides the medical device 502 with means for determining the pulse generator current $I_{PG}$:

$$I_{PG} = f_{OSC} \times [((C_{osc} \times V_{ref}) \times (M \times N \times R2))/(R1)]$$

Through data processing, the average pulse generator current over a period of time and the total charge depleted from the power source may be determined from the number of counted oscillations. This data processing is performed by circuitry, software programs, or a combination thereof in the medical device, the programmer device, a combination of the medical device and the programmer, or another processor.

The pulse generator current $I_{PG}$ is measured by placing the current sense resister R1 in series with the battery 512. Drawing the pulse generator current $I_{PG}$ through this sense resistor R1 results in a small voltage drop, $V_{SENSE}$. The resistance value of the current sense resistor R1 should be small enough so that it does not impede device performance, yet should be large enough so that the typical voltage drop $V_{SENSE}$ which appears across the resistor R1 can be easily measured or otherwise detected. Although a range of values may be used, a 250 ohm sense resistor R1 is suitable for a pulse generator load 514 that draws an average of 10 to 100 microamperes. This voltage drop is reproduced across a larger-valued resistor R2, such as a 250 k ohm resistor for example, to generate in the attenuated current 548. The voltage across the resistor R2 is substantially the same as the voltage across the resistor R1 due to the feedback applied by the operational amplifier 550 and transistor 555. Because of the larger resistance of the resistor R2, a smaller or attenuated current 548 flows through the resistor R2. The resulting current 548 is further attenuated by a factor of M×N using the two current mirror stages 554 and 556 to form the oscillator input current 538.

The oscillator input current 538 charges the capacitor 534 in a cyclic fashion from zero volts up to the reference voltage $V_{REF}$. A comparator 540 monitors the voltage across the capacitor 534 and discharges the capacitor 534 back to zero volts once the voltage reaches or approximately equals $V_{REF}$.

As provided earlier, the current source 544 includes an operational amplifier 550. The operational amplifier 550 should have sufficient dynamic range to accommodate the peak currents associated with the switched-mode power converters used in implantable devices. Furthermore, the operational amplifier 550 and attenuation circuitry should have sufficient bandwidth to track the rapid changes in current drawn by the medical device. Connecting a large bypass capacitor across the pulse generator load 514 serves to smooth out the current drawn directly from the battery 512, which effectively reduces the magnitude of current peaks and also spreads them out over time. Since both the voltage drop across R1 and the input offset voltage errors for an operational amplifier 550 can be on the order of a few millivolts, an operational amplifier offset voltage can cause substantial differences in voltages across resistors R1 and R2, and thus can introduce unacceptably large errors in the current measurement.

Figure 6:
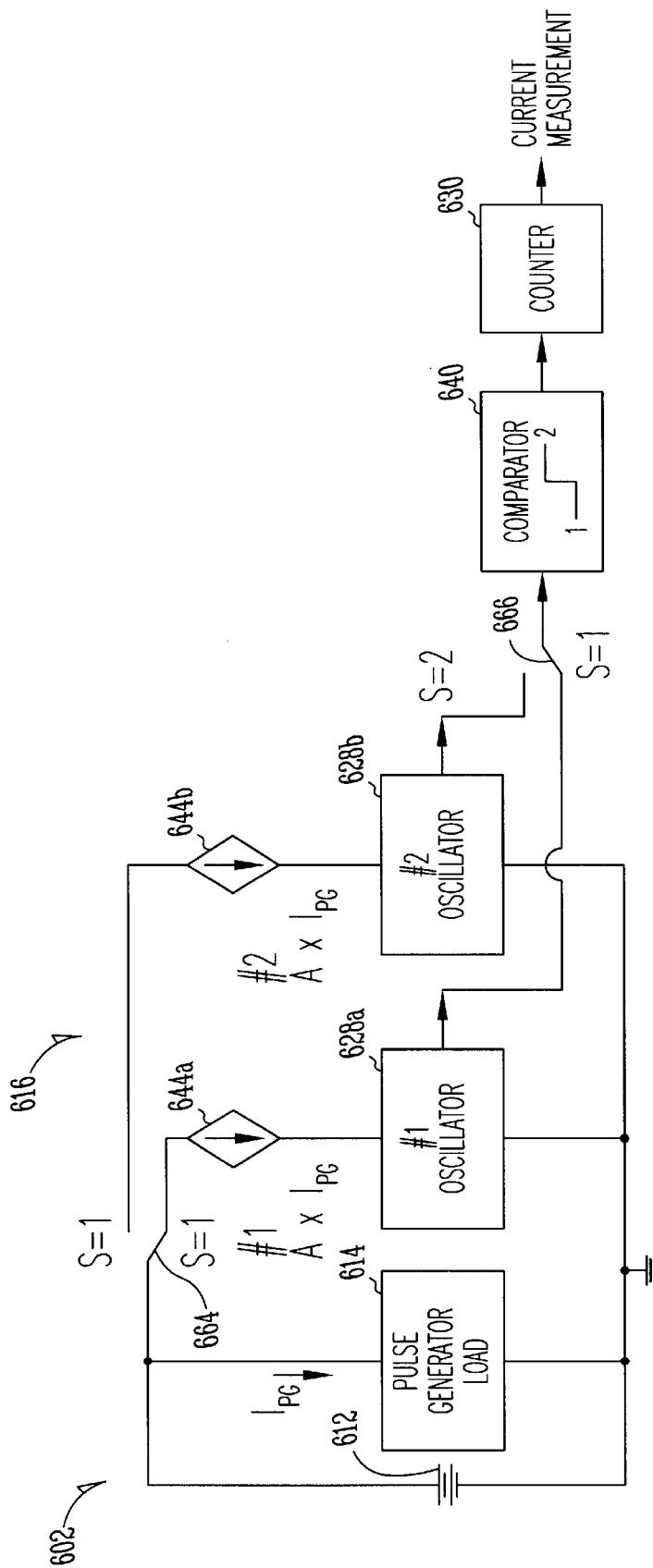
FIG. 6 is a block diagram of the electronic circuitry for the medical device of FIG. 2.

FIG. 6 shows a block diagram of another electronic circuitry embodiment for the medical device 602 of FIG. 2 adapted for controlling the offset (i.e. autozeroing). In particular, the block diagram shows that two current sources 644a and 644b are being used in the device 616 for measuring pulse generator current, wherein one of the current sources continues to operate in a fashion that allows the current measurement device 616 to continuously measure current as the other current source is calibrated. For example, in the case for current sources that incorporate operational amplifiers, one of the operational amplifiers may be autozeroed while the other operates normally. As shown in FIG. 6, separate oscillators 628a and 628b may be used in conjunction with the separate current sources 644a and 644b. The switches 664 and 666 cooperate to control whether the first circuit (S=1) or the second circuit (S=2) is measuring current.

Figure 7:
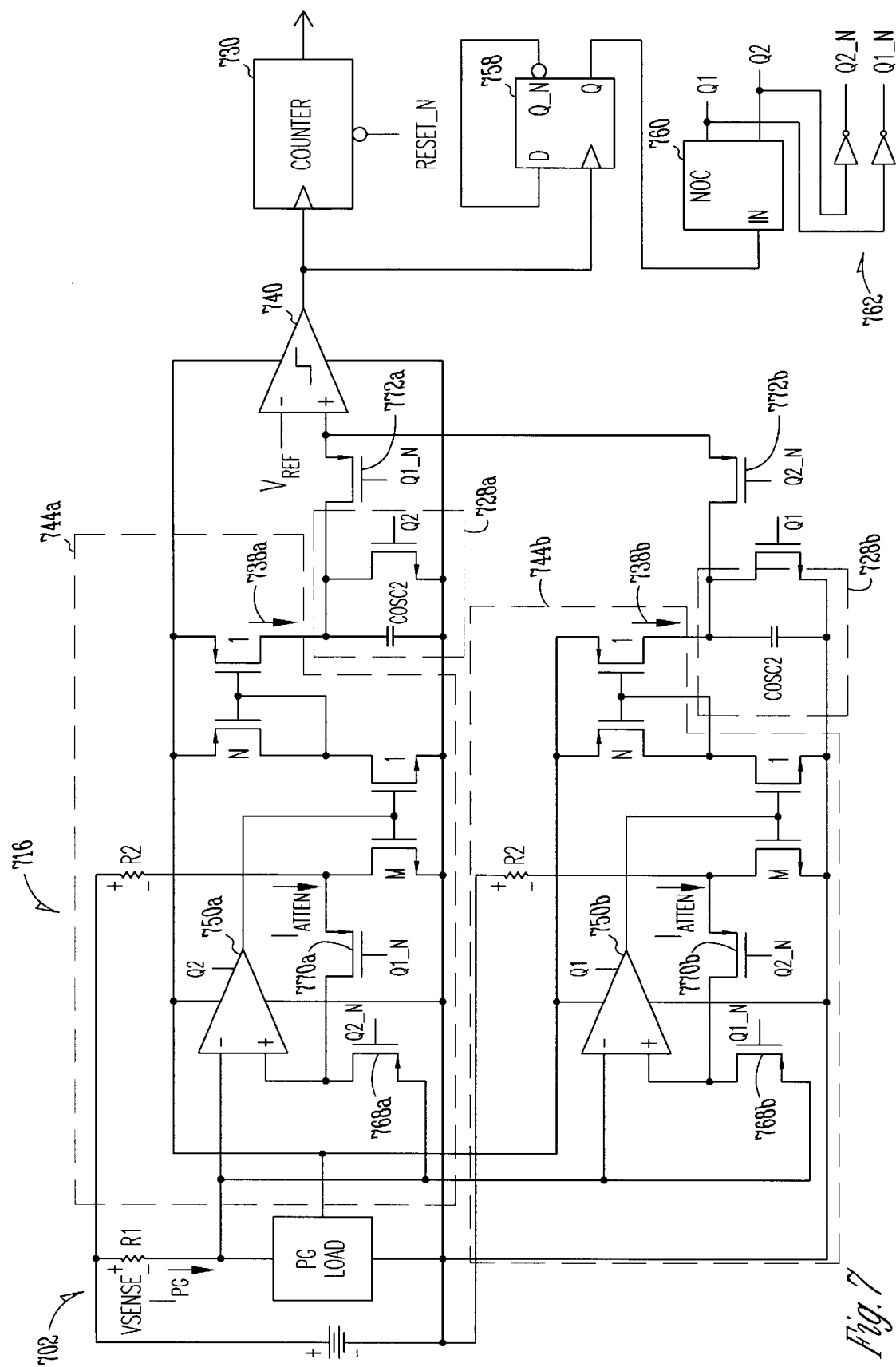
FIG. 7 is a schematic of the electronic circuitry according to the block diagram of FIG. 6.

FIG. 7 shows a schematic of an electronic circuitry embodiment according to the block diagram of FIG. 6. The autozeroed current measurement circuit attempts to eliminate any operational amplifier offset voltage errors from the current measurement. Since both the voltage drop across R1 and the input offset voltage errors for an operational amplifier can be on the order of a few millivolts, an operational amplifier offset voltage can cause substantial differences in voltages across resistors R1 and R2, and thus can introduce unacceptably large errors in the current measurement.

FIG. 7 shows two complementary circuits. Each one of these illustrated circuits includes a current source 744a and 744b with an operational amplifier 750a and 750b, and also includes an oscillator 728a and 728b. The operational amplifiers 750a and 750b have an autozeroing feature, as will be discussed in more detail below with respect to FIG. 8. Since an autozeroing or calibration function requires time to perform, a current measuring device 716 having a single current source cannot autozero, or otherwise calibrate, the current source while measuring the pulse generator current $I_{PG}$. Using two operational amplifiers 750a and 750b allows the device 716 to calibrate itself and still continuously measure current. For example, while the operational amplifier 750a in one of the current sources 744a is autozeroing to calibrate the current measurement device 716, the other current source 744b will continue to provide an oscillator input current 738b that is dependent on the pulse generator current $I_{PG}$. Thus, the circuit compensates for the offset voltages of the operational amplifiers 750a and 750b, and still continuously determines the pulse generator current $I_{PG}$.

The digital logic elements that appear on the right side of FIG. 7 are a D flip-flop 758, a non-overlapping clock generator 760, and a pair of inverters 762. The D flip-flop 758 acts as a toggle flip-flop that flips to the opposite logic state on every rising edge of the clock input. The non-overlapping clock generator 760 provides two complementary "non-overlapping active-high" outputs; i.e. provides two output signals (Q1 and Q2) that are essentially complementary but are never high at the same time. The inverters 762 generate complementary outputs. Thus, the digital logic elements provide Q1, Q1_N, Q2, and Q2_N that are used to control the overall functioning of the above-described circuits or circuit branches, wherein the "_N" suffix indicates that the logic signal is "active-low" and is used to turn on a PMOS device. When Q1 is high, the first current source 744a and oscillator circuit 728a are operating in a fashion to actively measure current, and the operational amplifier 750b in the second current source 744b is autozeroed. When Q2 is high, the second current source 744b and oscillator circuit 728b actively measures current, and the operational amplifier 750a in the first current source 744a is autozeroed.

Thus Q1, including the signals Q1 and Q1_N, generally represents a first state in which the first current source operates to measure current while the second current source is calibrated or autozeroed. Q2, including the signals Q2 and Q2_N, generally represents a second state in which the second current source operates to measure current while the first current source is calibrated or autozeroed. The circuit switches between these states, as previously illustrated by switch 664 and switch 666 of FIG. 6. FIG. 7 illustrates that switch 664 of FIG. 6 generally is formed by transistors 770a and 770b; and further illustrates that switch 666 of FIG. 6 generally is formed by transistors 772a and 772b. Transistors 768a and 768b, when actuated, effectively tie together the inputs of their respective operational amplifiers 750a and 750b for the autozeroing process.

Figure 8:
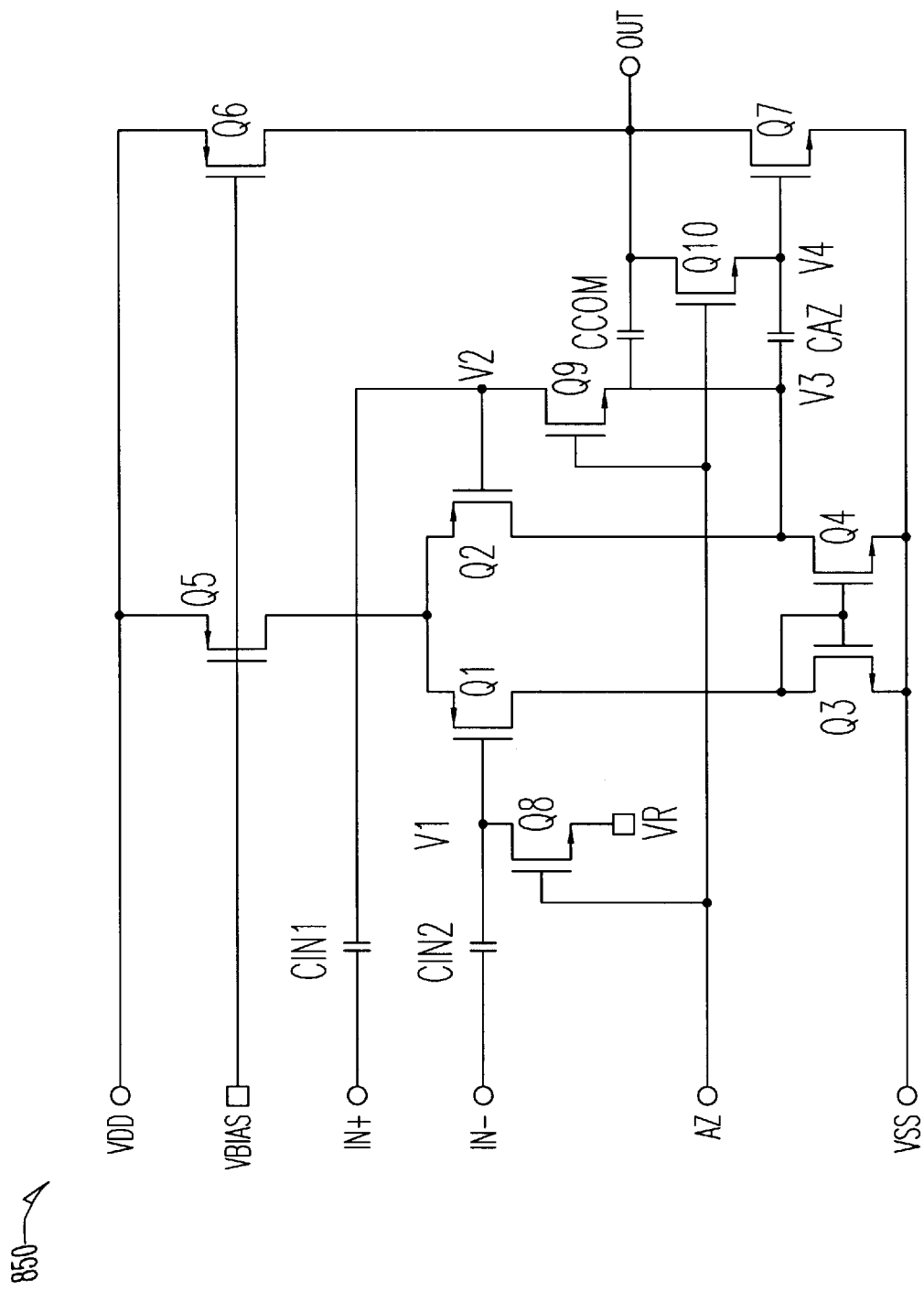
FIG. 8 is a schematic of an operational amplifier that has an autozero feature such as those that may be used in the electronic circuitry of FIG. 7.

FIG. 8 represents an operational amplifier with an autozeroing feature. The illustrated operational amplifier 850 is a two-stage, Miller-compensated operational amplifier with an autozero function. The capacitor "CCOM" provides stability. The first stage comprises the differential pair of transistors Q1 and Q2, which is supplied a bias current from transistor Q5, and which is actively loaded by the current mirror formed by the transistors Q3 and Q4. The second stage comprises the transistor Q7, which is actively loaded with the current-source transistor Q6.

The operational amplifier performs its autozero function when the "AZ" input is high, i.e. at logic 1. The autozero function is described below with respect to the operational amplifier schematic of FIG. 8. The inputs to the amplifier are effectively tied together by a PMOS transistor 768a or 768b, as illustrated in FIG. 7, which are activated when the corresponding circuit is autozeroed. Both of the operational amplifier inputs are capacitively coupled. The voltage V1 at the gate of Q1 is at a reference voltage VR through an actuated transistor QS, and the offset voltage V2 of the first stage is sampled onto capacitor CIN1 through an actuated transistor Q9. The capacitor CAZ capacitively couples the output of the first stage V3 to the input of the second stage V4. Transistor Q10 is actuated by the high AZ signal and causes the second stage transistor Q7 to be configured as an NMOS diode, which "self-biases" the second stage during autozeroing. After the "AZ" input goes low, i.e. at logic 0, the capacitor CAZ maintains the voltage V3–V4 that it sampled while the AZ input was held high.

The figures presented and described in detail above are similarly useful in describing the method aspects of the present subject matter. The methods described below are nonexclusive as other methods may be understood from the specification and the figures described above.

One aspect of the present subject matter provides a method for determining current drain for a medical device. In this method, an oscillating output is provided with a frequency of oscillation that is dependent on a pulse generator current $I_{PG}$. An oscillation count is provided or determined for the oscillating output, and the pulse generator current $I_{PG}$ is determined based on the oscillation count over the period of time. In one embodiment, the oscillating output is provided by charging a capacitor, comparing a voltage formed across the capacitor with a reference voltage $V_{REF}$, and discharging the capacitor when the voltage across the capacitor increases to a level equal to the reference voltage $V_{REF}$. In another embodiment, this method also includes providing an oscillator input current to the oscillator that is dependent on the pulse generator current $I_{PG}$. The oscillator input current is provided to the oscillator by dividing current drawn from a battery into the pulse generator current $I_{PG}$ and into an attenuated current that is dependent on the pulse generator current $I_{PG}$. The attenuated current is reduced to the oscillator input current.

Another aspect provides a method for tracking charge depletion of a battery or other power supply in an implantable medical device. In this method, an oscillating output is provided with a frequency of oscillation that is dependent on a pulse generator current $I_{PG}$. An oscillation count is determined or provided for the oscillating output over a period of time. The charge depletion of a battery is determined by continuously summing the oscillation count over successive periods of time. In one embodiment, the oscillating output is provided by charging a capacitor, comparing a voltage formed across the capacitor with a reference voltage $V_{REF}$, and discharging the capacitor when the voltage across the capacitor increases to a level equal to the reference voltage $V_{REF}$. In another embodiment, the method also includes providing an oscillator input current that is dependent on the pulse generator current $I_{PG}$. In another embodiment, the oscillator input current is provided to the oscillator by dividing current drawn from a battery into the pulse generator current $I_{PG}$ and into an attenuated current that is dependent on the pulse generator current $I_{PG}$, and reduces the attenuated current to the oscillator input current.

The system and method for measuring battery current, described herein, is incorporated into several applications. These applications include, but are not limited to, the following applications for determining battery status, for detecting potential faults, and for displaying current drain.

Battery Status

The battery current measurement device described above generates pulses, wherein each pulse represents a quantity of charge given by the equation:

$$Q = [(C_{osc} \times V_{ref}) \times (M \times N \times R2)]/R1.$$

If the pacemaker battery has a 1 Amp Hour capacity, it holds a charge of 3600 C; i.e. 1 A×60 min/hr×60 sec/min= 3600 C. If, as in the example provided above, R1 is 250 ohms, R2 is 250 k ohms, $V_{REF}$ is one volt, $C_{OSC}$ is 50 picofarads, and M×N=20, each counter pulse represents 1 $\mu C$ of charge. Therefore, in this example, the counter should count to $3.6 \times 10^9$, which corresponds to $(3600 \text{ C}) \times (1 \times 10^6 \text{ pulses/C})$. A 32-bit counter is appropriate as it corresponds to a value of $2^{32} = 4.294967296 \times 10^9$. The degree of battery depletion can then be determined directly from this count value by multiplying the count by the 1 $\mu C$ of charge contained in the capacitor.

However, it is unlikely that the charge depleted from the battery needs to be tracked to within 1 $\mu C$. Rather, only N of the most significant bits are needed to determine the charge count, wherein the value of N depends on the degree of precision desired for the battery depletion estimate. For example, to report the battery depletion as a percentage with 1% resolution, only the seven (N=7) most significant bits ($2^7=128$) of the charge counter need to be examined, which corresponds to a resolution of:

$$\frac{1}{128} \times \frac{2^{32}}{3.6 \times 10^9} = 0.93\%$$

A designer, with a view toward ensuring adequate safety margins that maintain acceptable device performance, selects battery depletion values for the pacemaker elective-replacement-time (ERT) and the end-of-life (EOL) indications. The battery depletion values for ERT and EOL may be viewed as a replacement percentage.

Fault Detection

Latent electrical faults within implanted pacemakers can often result in elevated battery current drain. Unfortunately, these types of failures can go undetected early on in the life of a device if a battery current measurement circuit is not available. To facilitate detection of these failures, the battery current measurement device described above can be employed.

An appropriate upper limit for the battery current, i.e. fault detection criterion, is determined in order to identify battery current drain that is excessive and thus indicative of an electrical fault within the device. For example, an embodiment that derives this upper limit from a worst-case estimate of the battery current drain over all possible operating conditions can result in an under-sensitive current fault detector. However, an embodiment that derives the upper limit from an "expected current drain" value is more sensitive to fault detection. The upper limit is compared against the actual current measurement value to determine whether a current fault exists. The "expected current drain" value can take into consideration the pace amplitude, the pulse width, the lead impedance, the pacing rate, and the paced-to-intrinsic ratio. A current fault is declared when:

$$I_{MEASURED} > (I_{EXPECTED} \times K) + I_{OFFSET}.$$

For example, if it is desired to declare a fault when the measured current value is in excess of twice the expected current value, K is set to 2 and $I_{OFFSET}$ is set to 0 $\mu A$. As another example, if it is desired to declare a fault when the measured current value exceeds the expected current value by 50 $\mu A$, K is set to 1 and $I_{OFFSET}$ is set to 50 $\mu A$.

The current measurement can be obtained once a fault detection criterion has been established. As described previously, the battery current measuring device generates a digital output pulse signal whose frequency is proportional to the battery current drain. The frequency of this pulse signal, and hence the battery current, is determined by counting the number of pulses that appear over a known time interval.

The time interval used to determine the frequency is chosen to provide optimal fault detection performance. Choosing a relatively large measurement smooths the normal minimum and maximum current extremes to an acceptable level. This time averaging is desirable because a battery current fault should not be triggered for the large current transients that are a normal part of operation for medical devices. In a pacemaker, for example, a fault should not be triggered when the pacing supply recharges immediately following the delivery of a pace. However, if the interval is too long, it becomes difficult or even impossible to localize intermittent fault conditions to a particular time.

Battery Current Reporting

The battery current measurement device is incorporated in an application for reporting the present current drain value back to the physician or clinician who is performing a medical device implant procedure or a follow-up evaluation. In order to obtain the current measurements, the clinician interrogates the device using an external programmer. The interrogation occurs through a communication channel, such as a telemetry channel. This telemetry activity typically requires significant battery current. Thus, an instantaneous or real-time current measurement during a telemetry session includes this additional telemetry current which is not present in normal day-to-day pacemaker operation.

Figure 9:
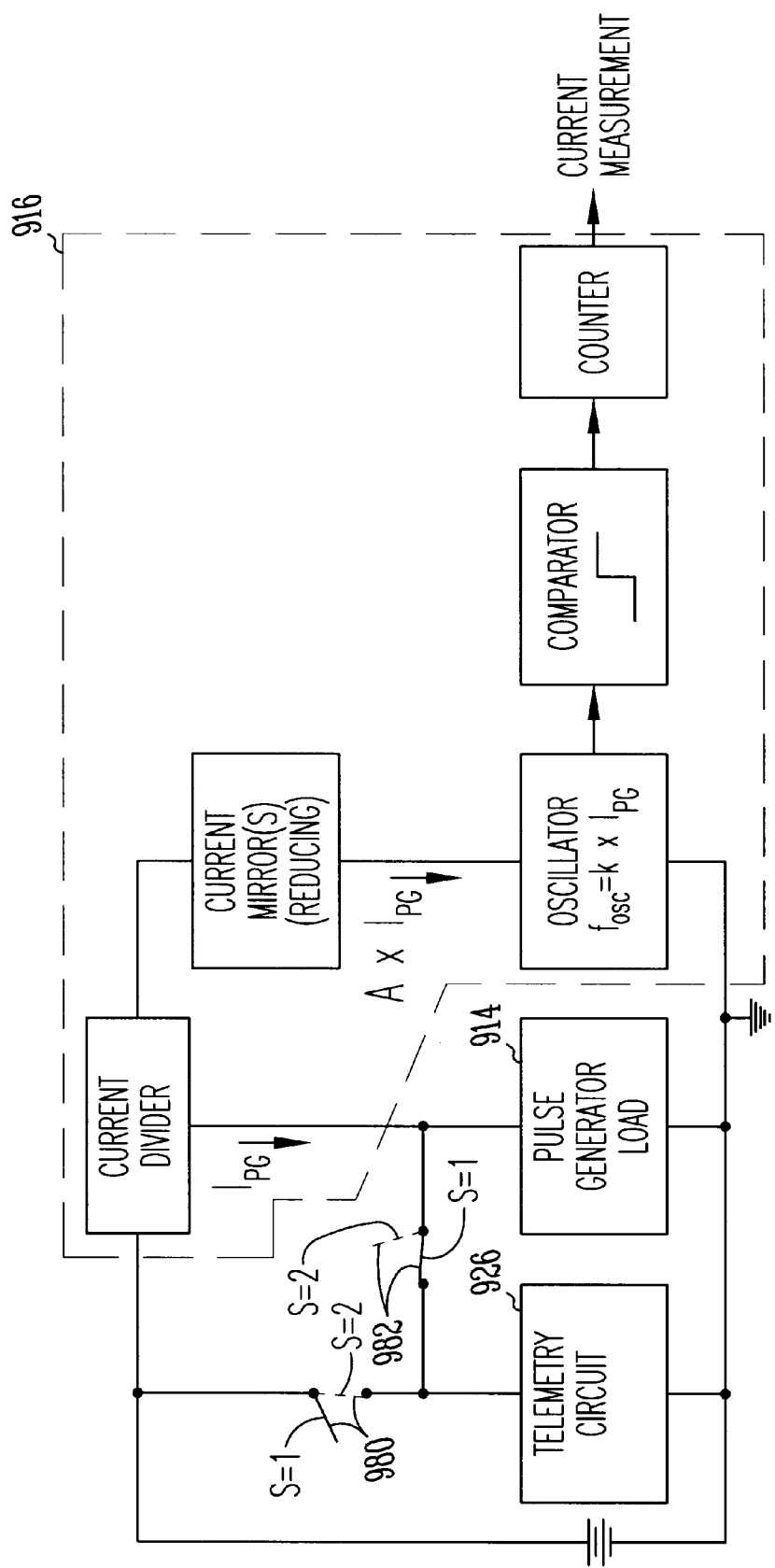
FIG. 9 is a block diagram of one embodiment of the electronic circuitry for the medical device of FIG. 2, wherein the current measuring device does not measure current drawn by the telemetry circuitry during telemetry sessions.

FIG. 9 is a block diagram of one embodiment of the electronic circuitry for the medical device of FIG. 2. To alleviate the above-described problem, the current measurement device 916 does not measure current drawn by the telemetry circuitry 926 during telemetry sessions. FIG. 9 shows two switches 980 and 982, and further shows that the two switches have a first state S=1 and a second state S=2. The electronic circuitry is typically in the first state S=1; i.e. a non-telemetry session. The switch 980 is open and the switch 982 is closed in the first state such that the quiescent current drawn by the telemetry circuit is included in the current $I_{PG}$. The switch 980 is closed and the switch 982 is open in the second state such that the higher current drawn by the telemetry circuit during a telemetry session is not included in the current $I_{PG}$.

This application is intended to cover any adaptations or variations of the present invention. It is manifestly intended that this invention be limited only by the claims and equivalents thereof.

What is claimed is:

1. A medical device, comprising:
   a battery;
   a pulse generator, wherein the pulse generator draws a pulse generator current from the battery;
   an electrode system in electrical communication with the pulse generator, wherein the electrode system applies electrical therapy to a patient; and
   a current measuring device for determining the pulse generator current, wherein the current measurement device is adapted for being calibrated while determining the pulse generator current.

2. The medical device of claim 1, wherein the pulse generator comprises:
   a processor;
   a memory portion operably connected to the processor;
   a pulse and sense portion operably connected to the processor and to the electrode system; and
   a communication portion operably connected to the processor for communicating with a programmer.

3. The medical device of claim 1, wherein the current measuring device produces an oscillating output with a frequency of oscillation that is dependent on the pulse generator current and provides an oscillation count from which the pulse generator current is determined.

4. The medical device of claim 1, wherein the current measuring device determines the average pulse generator current over a period of time.

5. The medical device of claim 1, wherein the current measuring device determines a total charge depleted from the battery.

6. The medical device of claim 1, wherein the current measurement device detects potential faults in the medical device by comparing a measured current drain against an expected current drain.

7. The medical device of claim 1, wherein:
   the current measurement device communicates with a programmer to report a measured pulse generator current;
   the current measurement device is connected to a communication circuit during inactive communication periods; and
   the current measurement device is disconnected from the communication circuit during active communication periods.

8. The medical device of claim 1, wherein the current measurement device includes:
   an oscillator for producing the oscillating output with a frequency of oscillation that is dependent on the pulse generator current; and
   a counter for providing an oscillator count from which the pulse generator current is determined.

9. The medical device of claim 8, wherein the oscillator comprises:
   a capacitor charged by an oscillator input current that is dependent on the pulse generator current; and
   a reset switch for discharging the capacitor when a voltage across the capacitor increases to a level equal to a reference voltage, wherein a resulting comparator output oscillates.

10. The medical device of claim 8, wherein the current measurement device further comprises a comparator for comparing a voltage across the capacitor with a reference voltage and providing a resulting comparator output to the counter.

11. The medical device of claim 8, wherein the counter is periodically reset using a known, stable time base.

12. The medical device of claim 8, wherein:
    the current measurement device further comprises at least two current sources that provide an oscillator input current;
    each of the current sources operates in a calibration state and a current measurement state; and
    one of the at least two current sources operates in the calibration state as the other of the at least two current sources operates in the current measurement state.

13. The medical device of claim 12, wherein each of the at least two current sources includes an operational amplifier having a feature for autozeroing an offset voltage.

14. A medical device, comprising:
    a battery;
    a pulse generator, wherein the pulse generator draws a pulse generator current from the battery;
    an electrode system in electrical communication with the pulse generator, wherein the electrode system applies electrical therapy to a patient; and
    a current measuring device for determining the pulse generator current, the current measurement device including:
       an oscillator for producing an oscillating output with a frequency of oscillation that is dependent on the pulse generator current;
       a counter for providing an oscillator count from which the pulse generator current is determined; and
       a current source for providing an oscillator input current to the oscillator that is dependent on the pulse generator current, wherein the current source includes a current divider for dividing current drawn from the battery into both the pulse generator current and an attenuated current.

15. The medical device of claim 14, wherein the current divider includes:
    a sense resistor through which the pulse generator current flows;
    an attenuation resistor through which the attenuated current flows; and
    an operational amplifier for providing substantially equal voltage drops across the sense resistor and across the attenuation resistor.

16. The medical device of claim 15, wherein:
    the current measurement device further comprises a second current source including a second operational amplifier;
    the operational amplifiers have a feature for autozeroing an offset voltage; and
    the current measuring device continuously measures current as one current source is autozeroed while the other current source continues to operate.

17. The medical device of claim 14, wherein the current source further includes at least one current mirror stage.

18. The medical device of claim 17, wherein the at least one current mirror stage includes:
    a first current mirror stage for receiving the attenuated current; and
    a second current mirror stage for providing the oscillator input current.

19. The medical device of claim 14, wherein the current source is adapted for providing the input current while being calibrated.

20. The medical device of claim 14, further comprising a pair of switches for selectively connecting a telemetry circuit to the current measurement device, wherein:
the pulse generator current includes a quiescent current drawn by the telemetry circuit during a non-telemetry session, and
the pulse generator current does not include a larger current drawn by the telemetry circuit during a telemetry session.

21. A device for determining a pulse generator current drawn from a battery of an implantable medical device, comprising:
a current source that provides an input current that is dependent on the pulse generator current, wherein the current source is adapted for providing the input current while being calibrated;
an oscillator for receiving the input current and producing an oscillating output, wherein the oscillating output has a frequency of oscillation dependent on the pulse generator current; and
a counter for providing an oscillation count for the oscillating output, wherein the pulse generator current is determined from the oscillation count.

22. The device of claim 21, wherein the current source includes a current divider for dividing current drawn from the battery into the pulse generator current and an attenuated current, the current divider including:
a sense resistor through which the pulse generator current flows;
an attenuation resistor through which the attenuated current flows; and
an operational amplifier for providing substantially equal voltage drops across the sense resistor and across the attenuation resistor.

23. The device of claim 22, wherein the operational amplifier further provides negative feedback.

24. The device of claim 22, further comprising a second current source including a second operational amplifier, wherein the operational amplifiers have a feature for autozeroing an offset voltage, and wherein one current source is autozeroing while the other current source continues to operate.

25. The device of claim 21, wherein the current source further includes at least one current mirror stage for performing a current reduction function.

26. A medical device, comprising:
a battery;
a pulse generator, wherein the pulse generator draws a pulse generator current from the battery;
an electrode system in electrical communication with the pulse generator, wherein the electrode system applies electrical therapy to a patient; and
a current measuring device for determining the pulse generator current, the current measurement device including:
an oscillator for producing an oscillating output with a frequency of oscillation that is dependent on the pulse generator current;
a counter for providing an oscillator count from which the pulse generator current is determined; and
a first and second current source for providing an oscillator input current to the oscillator that is dependent on the pulse generator current, wherein each current source includes a current divider for dividing current drawn from the battery into both the pulse generator current and an attenuated current, wherein the current divider includes:
a sense resistor through which the pulse generator current flows;
an attenuation resistor through which the attenuated current flows; and
an operational amplifier for providing substantially equal voltage drops across the sense resistor and across the attenuation resistor, wherein:
the operational amplifier further provides negative feedback; and
each operational amplifier has a feature for autozeroing an offset voltage such that the current measuring device continuously measures current as one current source is autozeroed while the other current source continues to operate.

27. A method for determining current drain for a battery-operated medical device, comprising:
providing an input current to an oscillator, wherein:
the input current is dependent on a pulse generator current; and
the oscillator responds to the input current by generating an oscillating output with a frequency of oscillation that is dependent on the pulse generator current;
providing an oscillation count for the oscillating output over a period of time; and
determining the pulse generator current based on the oscillation count over the period of time,
wherein providing an oscillating output with a frequency of oscillation that is dependent on a pulse generator current comprises:
charging a capacitor;
comparing a voltage formed across the capacitor with a reference voltage; and
discharging the capacitor when the voltage across the capacitor increases to a level equal to the reference voltage.

28. A method for determining current drain for a battery-operated medical device, comprising:
providing an input current to an oscillator, wherein:
the input current is dependent on a pulse generator current; and
the oscillator responds to the input current by generating an oscillating output with a frequency of oscillation that is dependent on the pulse generator current;
providing an oscillation count for the oscillating output over a period of time; and
determining the pulse generator current based on the oscillation count over the period of time,
wherein providing an oscillator input current to the oscillator that is dependent on the pulse generator current comprises:
dividing current drawn from a battery into the pulse generator current and into an attenuated current that is dependent on the pulse generator current; and
reducing the attenuated current to the oscillating input current.

29. A method for determining current drain for a battery-operated medical device, comprising:
providing an input current to an oscillator, wherein:
the input current is dependent on a pulse generator current; and
the oscillator responds to the input current by generating an oscillating output with a frequency of oscillation that is dependent on the pulse generator current;

providing an oscillation count for the oscillating output over a period of time; and determining the pulse generator current based on the oscillation count over the period of time, wherein:
providing an input current to an oscillator includes providing at least two current sources;

each of the at least two current sources operate in a current measurement state in which the current source is providing the input current that allows the pulse generator current to be determined, and further operate in a calibration state in which the current source is being calibrated; and one of the at least two current sources is operating in the current measurement state while the other of the at least two current sources is operating in the calibration state.

30. The method of claim 29, wherein:

each of the at least two current sources includes an operational amplifier having a feature for autozeroing an offset voltage; and the current sources are calibrated by autozeroing the offset voltage.

31. A method for tracking charge depletion of a battery in an implantable medical device, comprising:

providing an input current to an oscillator, wherein:
the input current is dependent on a pulse generator current drawn by the implantable medical device; and the oscillator responds to the input current by generating an oscillating output with a frequency of oscillation that is dependent on the pulse generator current;

providing an oscillation count for the oscillating output over a period of time; and determining the charge depletion of a battery by continuously summing the oscillation count over successive periods of time, wherein providing an oscillating output with a frequency of oscillation that is dependent on a pulse generator current comprises:
charging a capacitor;
comparing a voltage formed across the capacitor with a reference voltage; and
discharging the capacitor when the voltage across the capacitor increases to a level equal to the reference voltage.

32. A method for tracking charge depletion of a battery in an implantable medical device, comprising:

providing an input current to an oscillator, wherein:
the input current is dependent on a pulse generator current drawn by the implantable medical device; and
the oscillator responds to the input current by generating an oscillating output with a frequency of oscillation that is dependent on the pulse generator current;

providing an oscillation count for the oscillating output over a period of time; and determining the charge depletion of a battery by continuously summing the oscillation count over successive periods of time, wherein providing an oscillator input current to the oscillator that is dependent on the pulse generator current comprises:

dividing current drawn from a battery into the pulse generator current and into an attenuated current that is dependent on the pulse generator current; and reducing the attenuated current to the oscillating input current.

33. A method for tracking charge depletion of a battery in an implantable medical device, comprising:

providing an input current to an oscillator, wherein:
the input current is dependent on a pulse generator current drawn by the implantable medical device; and the oscillator responds to the input current by generating an oscillating output with a frequency of oscillation that is dependent on the pulse generator current;

providing an oscillation count for the oscillating output over a period of time; and determining the charge depletion of a battery by continuously summing the oscillation count over successive periods of time, wherein:
providing an input current to an oscillator includes providing at least two current sources;

each of the at least two current sources operate in a current measurement state in which the current source is generating the input current that allows the pulse generator current to be determined, and further operate in a calibration state in which the current source is being calibrated; and one of the at least two current sources is operating in the current measurement state while the other of the at least two current sources is operating in the calibration state.

34. The method of claim 33, wherein:

each of the at least two current sources includes an operational amplifier having a feature for autozeroing an offset voltage; and the offset voltage of the operational amplifier is autozeroed to calibrate the current source.

35. A method of determining battery status of an implantable medical device, comprising:

determining a total charge capacity for a battery of an implantable medical device;

determining a degree of precision for tracking charge depleted from the battery;

determining a replacement percentage;

tracking the charge depleted from the battery, including:
providing an input current to an oscillator, wherein:
the input current is dependent on a pulse generator current; and
the oscillator responds to the input current by generating an oscillating output with a frequency of oscillation that is dependent on the pulse generator current;

providing an oscillation count for the oscillating output over a period of time; and determining the pulse generator current based on the oscillation count over the period of time; and providing an indication when remaining charge in the battery equals the replacement percentage.

36. The method of claim 35, wherein:

providing an input current to an oscillator includes providing at least two current sources;

each of the at least two current sources operate in a current measurement state in which the current source is providing the input current that allows the pulse generator current to be determined, and further operate in a calibration state in which the current source is being calibrated; and one of the at least two current sources is operating in the current measurement state while the other of the at least two current sources is operating in the calibration state.

37. The method of claim 36, wherein:

each of the at least two current sources includes an operational amplifier having a feature for autozeroing an offset voltage; and the offset voltage of the operational amplifier is autozeroed to calibrate the current source.

38. A method of detecting potential faults within an implantable medical device, comprising:

determining an upper limit for current from a battery of the implantable medical device; and determining current drain from the battery, including:
 providing an input current to an oscillator, wherein:
  the input current is dependent on a pulse generator current; and
  the oscillator responds to the input current by generating an oscillating output with a frequency of oscillation that is dependent on the pulse generator current;
 providing an oscillation count for the oscillating output over a period of time; and
 determining the pulse generator current based on the oscillation count over the period of time.

39. The method of claim 38, wherein determining an upper limit for current comprises determining an expected current drain and calculating the upper limit based on the expected current drain.

40. The method of claim 38, wherein:

providing an input current to an oscillator includes providing at least two current sources;

each of the at least two current sources operate in a current measurement state in which the current source is generating the input current that allows the pulse generator current to be determined, and further operate in a calibration state in which the current source is being calibrated; and one of the at least two current sources is operating in the current measurement state while the other of the at least two current sources is operating in the calibration state.

41. The method of claim 40, wherein:

each of the at least two current sources includes an operational amplifier having a feature for autozeroing an offset voltage; and the current sources are calibrated by autozeroing the offset voltage.

42. A method of reporting drain current in an implantable medical device, comprising:

determining current drain from the battery using a current measurement circuit, including:
 providing an input current to an oscillator, wherein:
  the input current is dependent on a pulse generator current; and
  the oscillator responds to the input current by generating an oscillating output with a frequency of oscillation that is dependent on the pulse generator current;
 providing an oscillation count for the oscillating output over a period of time; and
 determining the pulse generator current based on the oscillation count over the period of time;

disconnecting a telemetry circuit from the current measuring circuit in preparation for a telemetry session;

interrogating the implantable medical device via telemetry; and upon completing the telemetry session, connecting the telemetry circuit to the current measuring circuit.

43. The method of claim 42, wherein:

providing an input current to an oscillator includes providing at least two current sources;

each of the at least two current sources operate in a current measurement state in which the current source is providing the input current that allows the pulse generator current to be determined, and further operate in a calibration state in which the current source is being calibrated; and one of the at least two current sources is operating in the current measurement state while the other of the at least two current sources is operating in the calibration state.

44. The method of claim 43, wherein:

each of the at least two current sources includes an operational amplifier having a feature for autozeroing an offset voltage; and the offset voltage of the operational amplifier is autozeroed to calibrate the current source.

* * * * *

UNITED STATES PATENT AND TRADEMARK OFFICE
CERTIFICATE OF CORRECTION

PATENT NO. : 6,584,355 B2 Page 1 of 1
APPLICATION NO. : 09/829825
DATED : June 24, 2003
INVENTOR(S) : Stessman It is certified that error appears in the above-identified patent and that said Letters Patent is hereby corrected as shown below:

On sheet 5 of 8, in Fig 6, delete "S=1" (between reference numerals "602" and "616")

and insert -- S=2 --, therefor.

Signed and Sealed this

Twenty-seventh Day of May, 2008

JON W. DUDAS
*Director of the United States Patent and Trademark Office*